(12) United States Patent
Herweck et al.

(10) Patent No.: US 7,572,245 B2
(45) Date of Patent: Aug. 11, 2009

(54) APPLICATION OF A THERAPEUTIC SUBSTANCE TO A TISSUE LOCATION USING AN EXPANDABLE MEDICAL DEVICE

(75) Inventors: Steve A. Herweck, Nashua, NH (US); Paul Martakos, Pelham, NH (US); Geoffrey Moodie, Hudson, NH (US); Roger Labrecque, Londonderry, NH (US); Theodore Karwoski, Hudson, NH (US); Trevor Carlton, Hudson, NH (US)

(73) Assignee: Atrium Medical Corporation, Hudson, NH (US)

( * ) Notice: Subject to any disclaimer, the term of this patent is extended or adjusted under 35 U.S.C. 154(b) by 412 days.

(21) Appl. No.: 10/942,764

(22) Filed: Sep. 15, 2004

(65) Prior Publication Data

US 2005/0106206 A1    May 19, 2005

Related U.S. Application Data

(60) Provisional application No. 60/503,359, filed on Sep. 15, 2003.

(51) Int. Cl.
*A61M 31/00* (2006.01)

(52) U.S. Cl. .................................................. 604/103.02

(58) Field of Classification Search ........... 604/103.02, 604/523, 381, 382, 264, 265, 103.01–103.09, 604/915, 916, 96.01, 104–109
See application file for complete search history.

(56) References Cited

U.S. PATENT DOCUMENTS 4,702,252 A    10/1987    Brooks et al.

(Continued)

FOREIGN PATENT DOCUMENTS

DE    10115740 A1    10/2002

(Continued)

OTHER PUBLICATIONS

Clauβ, Wolfram, et al., "No Difference Among Modern Contrast Media's Effect on Neointimal Proliferation and Restenosis After Coronary Stenting in Pigs," *Investigative Radiology*, vol. 38(12):743-749 (2003).

(Continued)

*Primary Examiner*—Manuel A Mendez
(74) *Attorney, Agent, or Firm*—Lahive & Cockfield, LLP; Kevin J. Canning; Sean D. Detweiler

(57) ABSTRACT

A non-polymeric or biological coating applied to radially expandable interventional medical devices provides uniform drug distribution and permeation of the coating and any therapeutic agents mixed therewith into a targeted treatment area within the body. The coating is sterile, and is capable of being carried by a sterile medical device to a targeted tissue location within the body following radial expansion. The therapeutic coating transfers off the medical device due in part to a biological attraction with the tissue and in part to a physical transference from the medical device to the targeted tissue location in contact with the medical device. Thus, atraumatic local tissue transference delivery is achieved for uniform therapeutic agent distribution and controlled bio-absorption into the tissue after placement within a patient's body with a non-inflammatory coating.

12 Claims, 5 Drawing Sheets

U.S. PATENT DOCUMENTS

| | | | |
|---|---|---|---|
| 4,824,436 A | 4/1989 | Wolinsky | |
| 4,941,877 A | 7/1990 | Montano, Jr. | |
| 5,041,125 A | 8/1991 | Montano, Jr. | |
| 5,049,132 A * | 9/1991 | Shaffer et al. | 604/101.02 |
| 5,087,244 A | 2/1992 | Wolinsky et al. | |
| 5,267,985 A | 12/1993 | Shimada et al. | |
| 5,282,785 A | 2/1994 | Shapland et al. | |
| 5,286,254 A | 2/1994 | Shapland et al. | |
| 5,295,962 A | 3/1994 | Crocker et al. | |
| 5,336,178 A | 8/1994 | Kaplan et al. | |
| 5,456,666 A | 10/1995 | Campbell et al. | |
| 5,458,568 A | 10/1995 | Racchini et al. | |
| 5,490,839 A | 2/1996 | Wang et al. | |
| 5,498,238 A | 3/1996 | Shapland et al. | |
| 5,499,971 A | 3/1996 | Shapland et al. | |
| 5,509,899 A | 4/1996 | Fan et al. | |
| 5,514,092 A | 5/1996 | Forman et al. | |
| 5,569,198 A | 10/1996 | Racchini | |
| 5,628,730 A | 5/1997 | Shapland et al. | |
| 5,634,899 A | 6/1997 | Shapland et al. | |
| 5,749,845 A | 5/1998 | Hildebrand et al. | |
| 5,800,392 A | 9/1998 | Racchini | |
| 5,807,306 A | 9/1998 | Shapland et al. | |
| 5,865,787 A | 2/1999 | Shapland et al. | |
| 5,902,266 A | 5/1999 | Leone et al. | |
| 6,048,332 A | 4/2000 | Duffy et al. | |
| 6,120,477 A | 9/2000 | Campbell et al. | |
| 6,146,358 A * | 11/2000 | Rowe | 604/103.02 |
| 6,206,916 B1 | 3/2001 | Furst | |
| 6,231,600 B1 | 5/2001 | Zhong | |
| 6,287,285 B1 | 9/2001 | Michal et al. | |
| 6,299,604 B1 | 10/2001 | Ragheb et al. | |
| 6,355,063 B1 | 3/2002 | Calcote | |
| 6,358,556 B1 | 3/2002 | Ding et al. | |
| 6,364,856 B1 | 4/2002 | Ding et al. | |
| 6,364,893 B1 | 4/2002 | Sahatjian et al. | |
| 6,364,903 B2 | 4/2002 | Tseng et al. | |
| 6,369,039 B1 | 4/2002 | Palasis et al. | |
| 6,451,373 B1 * | 9/2002 | Hossainy et al. | 427/2.25 |
| 6,491,938 B2 | 12/2002 | Kunz | |
| 6,500,174 B1 | 12/2002 | Maguire | |
| 6,541,116 B2 | 4/2003 | Michal et al. | |
| 6,544,223 B1 | 4/2003 | Kokish | |
| 6,610,035 B2 | 8/2003 | Yang et al. | |
| 6,616,650 B1 | 9/2003 | Rowe | |
| 6,641,611 B2 | 11/2003 | Jayaraman | |
| 6,730,064 B2 | 5/2004 | Ragheb et al. | |
| 6,758,847 B2 | 7/2004 | Maguire | |
| 6,808,536 B2 | 10/2004 | Wright et al. | |
| 6,918,927 B2 | 7/2005 | Bates et al. | |
| 2002/0082679 A1 | 6/2002 | Sirhan et al. | |
| 2003/0083740 A1 | 5/2003 | Pathak | |
| 2003/0204168 A1 * | 10/2003 | Bosma et al. | 604/103.02 |
| 2004/0039441 A1 | 2/2004 | Rowland et al. | |
| 2004/0137066 A1 | 7/2004 | Jayaraman | |
| 2004/0167572 A1 | 8/2004 | Roth et al. | |
| 2004/0230176 A1 | 11/2004 | Shanahan et al. | |
| 2004/0236278 A1 | 11/2004 | Herweck et al. | |
| 2005/0101522 A1 | 5/2005 | Speck et al. | |
| 2005/0106206 A1 | 5/2005 | Herweck et al. | |
| 2005/0154416 A1 | 7/2005 | Herweck et al. | |
| 2005/0159809 A1 | 7/2005 | Hezi-Yamit et al. | |
| 2005/0182485 A1 | 8/2005 | Falotico et al. | |

FOREIGN PATENT DOCUMENTS

| | | |
|---|---|---|
| EP | 1539267 A2 | 6/2005 |
| EP | 1557183 A1 | 7/2005 |
| WO | WO-99/27989 A1 | 6/1999 |
| WO | WO-00/12147 A1 | 3/2000 |
| WO | WO-00/40278 A1 | 7/2000 |
| WO | WO-01/15764 A1 | 3/2001 |
| WO | WO-01/24866 A1 | 4/2001 |
| WO | WO-02/22199 A2 | 3/2002 |
| WO | WO-02/076509 A2 | 10/2002 |
| WO | WO-03/028622 A2 | 4/2003 |
| WO | WO-03/039612 A1 | 5/2003 |
| WO | WO-2004/006976 A1 | 1/2004 |
| WO | WO-2004/028582 A1 | 4/2004 |
| WO | WO-2004/028610 A2 | 4/2004 |

OTHER PUBLICATIONS

Salu, K.J., et al., "Latrunculin A inhibits smooth muscle cell proliferation adn neointimal formation in a porcine coronary stent model," *European Heart Journal*, vol. 4:143 (2002).

Scheller, Bruno, et al., "Addition of Paclitaxel to Contrast Media Prevents Restenosis After Coronary Stent Implantation," *Journal of the American College of Cardiology*, vol. 42(8):1415-1420 (2003).

Scheller, Bruno, et al., "Paclitaxel Balloon Coating, a Novel Method for Prevention and Therapy of Restenosis," *Circulation*, vol. 110:810-814 (2004).

Scheller, B., et al., "Intracoronary paclitaxel added to contrast media inhibits in-stent restenosis of porcine coronary arteries,"*European Heart Journal*, vol. 4:188 (2002).

Scheller, B., et al., "Lack of cardiotoxicity after intracoronary paclitaxel application,"*European Heart Journal*, vol. 4:295 (2002).

Scheller, B., et al., "Short-term exposure of vascular smooth muscle cells (VSMC to a contrast medium-paclitaxel formulation inhibits proliferation in vitro,"*European Heart Journal*, vol. 4:536 (2002).

Scheller, Bruno, "Paccocath ISR I trial," Euro PCR05 presentation.

van der Giessen, Wim, "Glimpse into the future—Part II, Beyond the DES, A Nitric Oxide Eluting System," Euro PCR, presentation.

International Search Report Application No. PCT/US04/30173, dated Mar. 8, 2006.

A paper entitled, "Evaluation of the Biocompatibility and Drug Delivery Capabilities of Biological Oil Based Stent Coatings," by Li, Shengqiao of the Katholieke Universiteit Leuven.

International Search Report for Application No. PCT/US04/30541, dated Apr. 17, 2006.

International Search Report for Application No. PCT/US2008/061419, dated Sep. 29, 2008.

* cited by examiner

APPLICATION OF A THERAPEUTIC SUBSTANCE TO A TISSUE LOCATION USING AN EXPANDABLE MEDICAL DEVICE

RELATED APPLICATIONS

This application claims priority to, and the benefit of, U.S. Provisional Application No. 60/503,359, filed Sep. 15, 2003, for all subject matter common to both applications. This application is being filed concurrently with U.S. patent application Ser. No. 10/943,075, which claims priority to U.S. Provisional Application No. 60/503,357, filed Sep. 15, 2003. The disclosures of all of the above-mentioned applications are hereby incorporated by reference herein in their entirety.

FIELD OF THE INVENTION

The present invention relates to therapeutic agent delivery, and more particularly to a device and/or system for delivering a therapeutic agent to a targeted tissue location within a patient to maximize the drug distribution and cellular uptake by the tissue atraumatically.

BACKGROUND OF THE INVENTION

Mechanical drug and agent delivery devices are utilized in a wide range of applications including a number of biological applications, such as catheter interventions and other implantable devices used to create a therapeutic or other biological effect within the body. Often, such delivery devices take the form of radially expandable devices used to mechanically open an occluded or narrowed blood vessel. For example, inflatable non-elastomeric balloons have been utilized for treatment of body passages occluded by disease and for maintenance of the proper position of catheter-delivered medical devices, such as stents, within such body passages. With the use of drug carrying polymers applied to the stents to form drug eluting stents, such stents are placed within body lumens with drugs or agents embedded therein for release of the drug or agent within the body.

Some intervention balloon catheters are made to deliver a systemic bolus of liquid or gas that includes a drug, to a targeted tissue location within the body using an open catheter lumen or channel located at some length along the catheter shaft. Unfortunately, when such systemic delivery means are used to deliver a controlled volume of medication to a desired tissue location, a majority of the medication is lost to systemic circulation because of an inability of the drug to quickly penetrate local tissue. Generally, most liquid formulations containing a drug or agent that is delivered to the targeted tissue location by liquid bolus does not penetrate the tissue sufficiently at the targeted tissue location to result in a significant therapeutic effect, and is consequently washed away by body fluids. This systemic dilution substantially diminishes the effectiveness of the drugs or agents provided through such delivery devices, and increases the likelihood of a greater systemic effect caused by the large quantity of drug or agent washed into the bloodstream. To compensate for such delivery inefficiency, the dose of drugs or agents must be volumetrically increased in anticipation that they will be principally washed away before therapeutically effecting the localized or targeted tissue area. However, because of the risk of increased systemic effects and possibly toxic overload, the volume of the drugs or agents must not exceed that which can still be considered safe for exposure by systematic dilution and subsequent systematic distribution throughout the patient's body. The drug or agent used in such an intervention delivery method must be safe enough in its diluted state to be washed away to other parts of the patient's body and not have unwanted therapeutic or otherwise detrimental effects. There is a delicate balance between making the drugs or agents sufficiently concentrated to have therapeutic characteristics at the targeted tissue location, while also being sufficiently diluted to avoid harmful effects after being washed away into the body's systemic circulation.

A further drug and agent delivery vehicle conventionally includes drug eluting stents. It is has been demonstrated that the localized concentration of drug permeation into tissue varies with the existing stent delivery vehicles, depending upon the drug load, drug dose, and release profile of such polymeric stent coatings used to carry and release the therapeutic agents after permanent stent device deployment. The drug concentrations at the struts of the stents are relatively higher than drug concentrations at areas between the struts of the stents. This can adversely affect the therapeutic effect of the drug. More specifically, there can be toxic drug concentrations in some areas of the tissue, while there are inadequate concentrations in other areas. Furthermore, the distribution of the drug by the stent to the tissue occurs only along the struts of the stent. If the generally cylindrical shape of a stent represents a total surface area of 100%, the actual location of the struts that form the stent after expansion deployment typically represents less than 20% of the surface area of the total cylindrical shape. Even if the surface area of the struts represented greater than 20% after radial expansion. the remaining portions of the cylindrical shape still would remain porous with a majority of large openings in the cylindrical stent geometry. The drug can only be transferred in those locations where the struts exist. Thus, with a conventional stent there are large sections where the drug cannot exist and cannot make direct contact with the tissue. After conventional drug eluting stent deployment, wherein a first small diameter slotted tube is inserted into the targeted organ space and expanded to a larger second diameter, the slotted tube becomes mostly open during the strut plastic deformation. Therefore, the large open sections of a deployed stent do not provide any means for delivering medication between the struts, or any means for the drug to be transferred into the tissue.

SUMMARY

There is a need for a therapeutic coating for medical devices able to be atraumatically transferred from the medical device to targeted tissue locations within the body without causing an inflammatory response and while delivering a therapeutic agent. The present invention is directed toward further solutions to address this need.

In accordance with one example embodiment, a medical device includes a body having an exterior surface. A therapeutic coating is disposed on at least a portion of the exterior surface. The therapeutic coating is compositioned to adhere to the exterior surface of the medical device while the medical device is positioned proximal to a targeted tissue location within a patient, and then transfer to the targeted tissue location upon contact between the therapeutic coating and the targeted tissue location to create an atraumatic therapeutic effect.

In accordance with aspects of the present invention, the therapeutic coating is formed of fatty acids including omega-3 fatty acids. A therapeutic agent can be emulsified in the therapeutic coating. A therapeutic agent can be suspended in the therapeutic coating. The therapeutic coating can be at least partially hydrogenated.

The therapeutic coating can further include at least one of a non-polymeric substance, a binder, and a viscosity increasing agent to stabilize the therapeutic mixture. The therapeutic coating can further include a solvent. Prior to implantation, the therapeutic coating can be a solid or a soft solid. Upon implantation, the therapeutic coating can maintain a soft solid, gel, or viscous liquid consistency; such that the therapeutic coating can be atraumatically smeared at the targeted tissue location, but not wash away.

In accordance with further aspects of the present invention, the medical device includes at least one of an endovascular prosthesis, an intraluminal prosthesis, a shunt, a catheter, a surgical tool, a suture wire, a stent, and a local drug delivery device.

In accordance with one embodiment of the present invention, a method of applying a therapeutic coating to a targeted tissue location includes applying the therapeutic coating to a medical device. The medical device is positioned proximal to a targeted tissue location within a patient. The therapeutic coating is smeared against the targeted tissue location, thus transferring at least a portion of the therapeutic coating to adhere to the targeted tissue location.

The method can further include removing the medical device. Alternatively, the medical device can be left as an implant at the targeted tissue location.

In accordance with further aspects of the method of the present invention, the therapeutic coating can include fatty acids including omega-3 fatty acids. A therapeutic agent can be emulsified in the therapeutic coating. A therapeutic agent can be suspended in the therapeutic coating. The therapeutic coating can be at least partially hydrogenated. The therapeutic coating can further include at least one of a non-polymeric substance, a binder, and a viscosity increasing agent to stabilize the therapeutic mixture The therapeutic coating can further include a solvent. Prior to implantation, the therapeutic coating can be a solid or a soft solid. Upon implantation, the therapeutic coating can maintain a soft solid, gel, or viscous liquid consistency; such that the therapeutic coating can be atraumatically smeared at the targeted tissue location but not wash away.

In accordance with further aspects of the method of the present invention, the medical device includes at least one of an endovascular prosthesis, an intraluminal prosthesis, a shunt, a catheter, a surgical tool, a suture wire, a stent, and a local drug delivery device. A plurality of medical devices can be utilized during a procedure to apply the therapeutic coating.

In accordance with one embodiment of the present invention, a method of applying a first therapeutic coating, a second therapeutic coating, and a third therapeutic coating to a targeted tissue location within a patient includes providing a first medical device with the first therapeutic coating. The first medical device is positioned in proximity with the targeted tissue location. The first medical device is radially expanded against the targeted tissue location, while simultaneously smearing the first therapeutic coating against the targeted tissue location. The first medical device is deflated or de-expanded and removed. A second medical device is provided with the second therapeutic coating, wherein the second medical device includes a balloon portion and a stent portion. The second medical device is positioned in proximity with the targeted tissue location. The second medical device is radially expanded against the targeted tissue location, while simultaneously smearing the second therapeutic coating against the targeted tissue location. It should be noted that the second therapeutic coating is applied not only at the location of stent struts, but also in-between struts where the balloon portion pushes the second therapeutic coating through to the targeted tissue location. The balloon portion of the second medical device is deflated and removed. A third medical device is provided with the third therapeutic coating. The third medical device is placed in proximity with the targeted tissue location. The third medical device is radially expanded against the targeted tissue location, while simultaneously smearing the third therapeutic coating against the targeted tissue location. The third medical device is deflated or de-expanded and removed.

In accordance with one example embodiment of the present invention, a balloon catheter includes a body having an exterior surface. A therapeutic coating can be disposed on at least a portion of the exterior surface. The therapeutic coating is compositioned to adhere to the exterior surface of the balloon catheter while the balloon catheter is positioned proximal to a targeted tissue location within a patient, and then transfer to the targeted tissue location upon contact between the therapeutic coating and the targeted tissue location at the time of radial expansion to create an atraumatic therapeutic effect. The balloon catheter can be a PTCA balloon catheter.

In accordance with one example embodiment of the present invention, a method of applying a therapeutic coating to a targeted tissue location includes applying the therapeutic coating to a balloon catheter. The balloon catheter is positioned proximal to a targeted tissue location within a patient in a first interventional procedure. The therapeutic coating is smeared against the targeted tissue location, thus transferring at least a portion of the therapeutic coating to adhere to the targeted tissue location during expansion of the balloon catheter. The balloon catheter is removed from the patient.

In accordance with one aspect of the present invention, the above method further includes applying the therapeutic coating to a second balloon catheter and a stent. The second balloon catheter and the stent are positioned proximal to the targeted tissue location within the patient in a second interventional procedure. The therapeutic coating is smeared against the targeted tissue location, thus transferring at least a portion of the therapeutic coating to adhere to the targeted tissue location during expansion of the balloon catheter. It should again be noted that the therapeutic coating is applied not only at the location of stent struts, but also in-between struts where the balloon portion pushes the therapeutic coating through to the targeted tissue location. The second balloon catheter is removed from the patient, leaving the stent.

In accordance with another aspect of the present invention, the above method can further include applying the therapeutic coating to a third balloon catheter. The third balloon catheter can be positioned proximal to the targeted tissue location within the patient in a third interventional procedure. The therapeutic coating can be smeared against the targeted tissue location, thus transferring at least a portion of the therapeutic coating to adhere to the targeted tissue location and the deployed stent during expansion of the third balloon catheter. The third balloon catheter can be removed from the patient.

BRIEF DESCRIPTION OF THE DRAWINGS

The present invention will become better understood with reference to the following description and accompanying drawings, wherein.

DETAILED DESCRIPTION

Figure 1A:
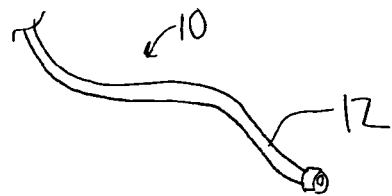
FIGS. 1A, 1B, 1C, 1D, 1E, 1F, and 1G are perspective illustrations of a variety of medical devices according to aspects of the present invention.
Figure 1B:
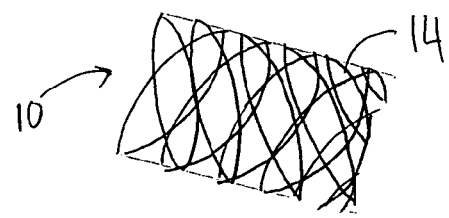
Figure 1C:
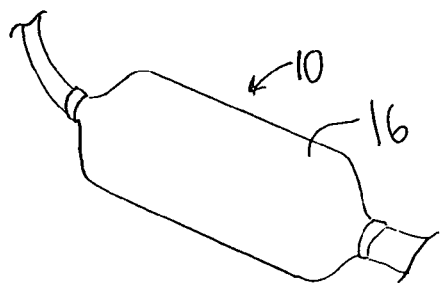
Figure 1D:
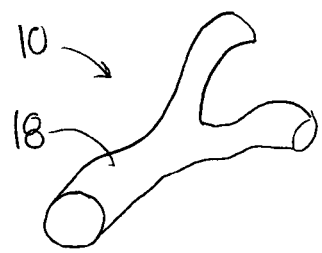
Figure 1E:
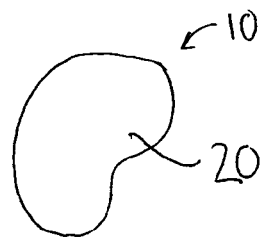
Figure 1F:
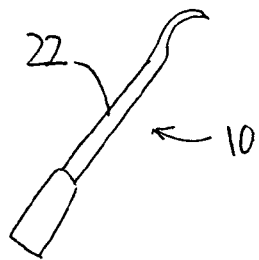
Figure 1G:
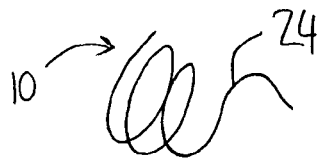

An illustrative embodiment of the present invention relates to use of a non-polymeric or biological coating that has been made to deliver a therapeutic agent or drug when applied to interventional medical devices for uniform drug distribution and cellular uptake into a targeted treatment area within the body. The present invention makes use of a sterile non-polymeric coating capable of being carried by a sterile medical device to a targeted tissue location within the body following radial expansion. The therapeutic coating transfers off the medical device without causing trauma to the local tissue being treated due in part to a biological attraction and in part to a physical transference from the medical device to the targeted tissue location in contact with the medical device. Thus, the present invention provides a local tissue transference delivery for uniform therapeutic agent distribution and controlled bio-absorption into the tissue after placement within a body cavity, organ, or tissue of a patient in a manner considered to be atraumatic to the targeted tissue location. Furthermore, the biological coating does not induce a chronic inflammatory response to the tissue after re-absorption or drug release. The type of medical device to which the therapeutic substance is applied can vary, as can the method of application of the non-polymeric biological coating to the medical device, and the method of substance transference of the non-polymeric coating from the medical device carrier and into the tissue of the body can also vary in addition to the mode of therapeutic agent release kinetics out from the biological substance and indo the tissue vary. In addition, the present invention has application in a number of different therapeutic blood vessel reperfusion techniques, including angioplasty, stent deployment, transcatheter balloon irrigation, angiography, embolic protection procedures, and catheter interventions.

FIGS. 1A through 6, wherein like parts are designated by like reference numerals throughout, illustrate example embodiments of an application of a therapeutic coating to using a medical device to a targeted tissue location within a patient, according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed in a manner still in keeping with the spirit and scope of the present invention.

The phrase "therapeutic drug and/or agent", "therapeutic coating", and variations thereof, are utilized interchangeably herein to indicate single drug or multiple therapeutic drugs, single or multiple therapeutic agents, or any combination of single or multiple drugs, agents, or bioactive substances. Such drugs or agents include, but are not limited to, those listed in Table 1 below herein. As such, any subtle variations of the above phrase should not be interpreted to indicate a different meaning, or to refer to a different combination of drugs or agents. The present invention is directed toward improved transference delivery of therapeutic drugs and/or agents, or any combination thereof, as understood by one of ordinary skill in the art.

It has been found, surprisingly, that certain biological oils and fats temporarily adhere sufficiently strong enough to both a temporary and permanently placed intraluminal medical device so that most of the biological coating remains on the intraluminal device as it is inserted into an internal body cavity, passageway, or tissue space of a patient. Once the medical device is positioned within the body of the patient, the oil or fat, with the therapeutic agents or ingredients contained thereto, can be transferred directly into the targeted tissue by the lipophilic absorptive action of the biological oil and fat. The natural attraction and cellular uptake of the oil and fat by the tissue causes an unexpected benefit for efficient drug permeation and delivery of the targeted treatment area within the body. As with any localized drug delivery system, maximizing drug permeation to the tissue treatment area without incurring high dose systemic load to the outer surface of the cell membrane is considered the ideal method of choice. Use of a biological oil or fat that has been carefully mixed with a drug ingredient has been found to substantially improve the effective penetration of the drug ingredient into local tissue by bio-absorption of the oil drug complex. Because of the biological attraction of the oil and fat complex is high for many tissues within the body, the oil and fat complex readily transfers from the medical device chemically intact, without need for a secondary biochemical reaction or biological reaction to remove the oil and fat coating from the medical device. The therapeutic oil and fat complex readily transfers off the medical device when engaged tightly to a targeted tissue location with sufficient dwell time to allow the coated medical device to remain in close contact with the tissue for a short period of time. Once the coated device becomes adequately engaged with the targeted treatment zone, the oil and or fat complex readily transfers off during radial expansion of the medical device with the therapeutic ingredients intact, directly onto the contacted tissue with limited systemic effect.

It has further been found that certain oils and fats can permeate the tissue of a patient more rapidly than other materials can penetrate the tissue. More specifically, if a targeted tissue location within a body cavity requires the application of a therapeutic, agent, the therapeutic agent can be applied to the targeted tissue location using a variety of different methods. The permeation of the tissue at the targeted tissue location by the therapeutic agent can be improved by mixing the therapeutic agent with a biological oil or fat, which permeates the tissue more efficiently than most therapeutic agents alone. When a therapeutic agent has been carefully solubilized, saturated or mixed without polymerizing the agents into the oil or fat, such a therapeutic complex allows the medication to adequately permeate the tissue cause a therapeutic response to the tissue. By chemically stabilizing the active ingredients into the oil or fat without chemical polymerization of the oil, fat and or drug ingredient, the complex sufficiently delivers a dose of medication or drug directly into the tissue. Thus, a mixture of an oil or fat and a therapeutic agent, without any chemical bonds formed between the oil or fat and the therapeutic agent, allows a medication to be more efficiently delivered in a form suitable for permeation into the tissue when engaged within a patient than local medication delivery without the presence of a non-polymerized oil or fat complex.

Rather than reliance upon a chemical bond between drug ingredient and the carrier, selected biological fats and oils allow the therapeutic agents to solubilize, mix, or be carried intact within the oil or fat to form an atraumatic therapeutic delivery complex. The therapeutic agent can further be nanoparticlized, dissolved, emulsified, or otherwise suspended within the oil or fat, enabling the therapeutic agents to be simultaneously absorbed by the tissue during the oil and fat absorption by the tissue.

It has been found experimentally that use of an oil or fat reduces the likelihood of there being an inflammatory reaction caused by the introduction of the therapeutic agent to the cells when exposed to the oil and fat complex. It is known that certain oils and fats, such as omega 3 fatty acids, are not only well received by body tissue, but have exhibited their own therapeutic and bioactive benefits. Such oils and fats reduce the otherwise common occurrence of an inflammatory reaction caused by the mechanical contact with the local tissue by the introduction of a mechanical delivery device, prosthesis, and/or therapeutic agent or medication. By mixing the therapeutic agent with the oil or fat, such inflammatory reactions are greatly reduced, thus improving the outcome of cellular uptake of the therapeutic agent into the tissue and the agent's biological effect. Furthermore, the oil or fat delivery system improves cellular uptake of the therapeutic agent during absorption of the smeared therapeutic coating.

Taking into account the ability of the oil or fat to perform as characterized above, the present invention includes a method and device for therapeutically treating the entire engagement area of targeted treatment zone. Example tissues can include a treatment zone within a blood vessel, a trachea, esophagus, urethra, or prostate lumen, and/or any engagement tissue location within the body. The localized treatment method involves engaging a transferable biological oil or fat, combined with an active therapeutic agent or series of medications, including non-polymeric substances, which are engaged to a targeted treatment zone within the body by catheter intervention steps or device deployment methods used in radial expansion medical device intervention procedures. In addition, this invention applies more generally to medical device intervention procedures within the body, and the local application of the therapeutic coating to a targeted treatment zone during such intervention procedures.

In accordance with one example embodiment of the present invention, a medical device 10 is provided for application thereto of a therapeutic coating. The medical device can be any number of devices that have application within a patient. For example, as shown in FIGS. 1A through 1G, the medical device 10 can include a catheter 12 (such as a Foley catheter, suction catheter, urethral catheter, perfusion catheter, PTCA catheter, and the like), a stent 14, a radially expandable device 16 (such as a catheter balloon, or a stent), a graft 18, a prosthesis 20, a surgical tool 22, a suture wire 24, or any other device or tool that makes contact with, or is proximal to, a targeted tissue location within a body cavity or body lumen.

For purposes of the remaining description, a particular embodiment of the present invention makes use of the radially expandable device 16 connected to the catheter 12, as utilized in conjunction with the stent 14, for an angioplasty type of procedure. However, it should be noted that the present invention is not limited to the particular system and method as described herein, but rather has application to a number of different medical devices 10 as identified above. It should furthermore be noted that the remaining description focuses on an angioplasty application of the above medical devices in combination with the therapeutic coating. However, the present invention is likewise not limited to angioplasty procedures, but rather is applicable in a number of different medical procedures making use of the above-identified medical devices 10.

Figure 2:
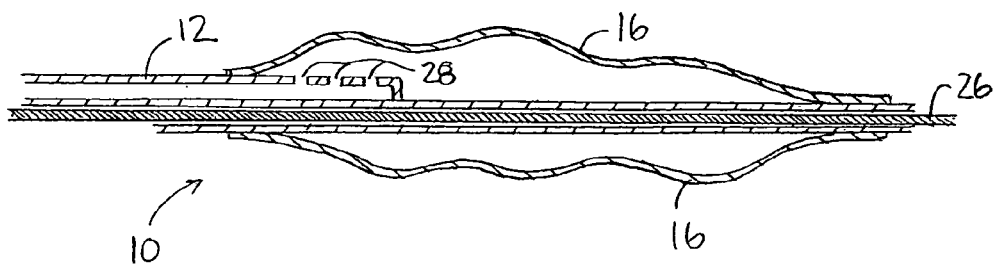
FIG. 2 is a diagrammatic cross-sectional view of a deflated radially expandable device, according to one aspect of the present invention.
Figure 3:
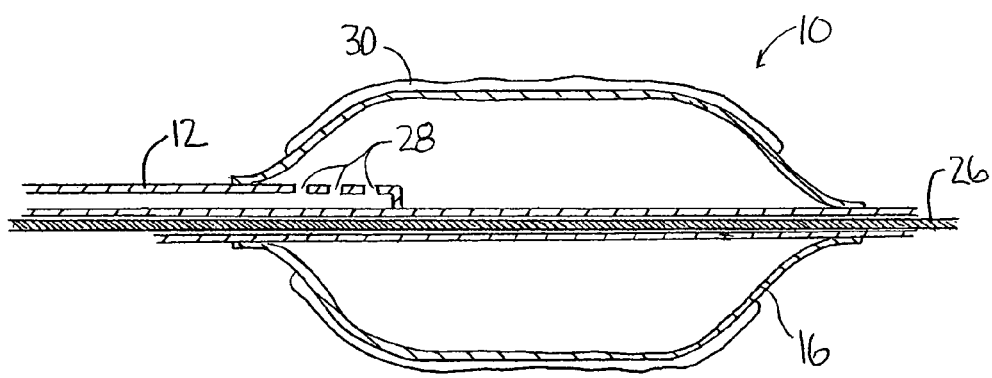
FIG. 3 is a diagrammatic cross-sectional view of the radially expandable device of FIG. 2 in expanded configuration, according to one aspect of the present invention.

In accordance with one example embodiment of the present invention, a radially expandable device 16 is constructed of a generally inelastic, polyester nylon blend material as illustrated in FIGS. 2 and 3. A catheter 12 and radially expandable device 16 are provided as shown in FIG. 2. The catheter 12 includes a guide wire 26 for guiding the catheter 12 and radially expandable device 16 to the body lumen. The catheter 12 has a number of openings 28 for providing a fluid to inflate the radially expandable device 16. FIG. 3 shows the radially expandable device 16 inflated.

Radially expandable devices provided by the present invention are suitable for a wide range of applications including, for example, a range of medical treatment applications within the body. Exemplary biological applications include use as a catheter balloon for treatment of implanted vascular grafts, stents, a permanent or temporary prosthesis, or other type of medical implant, used to treat a targeted tissue within the body, and treatment of any body cavity, space, or hollow organ passage(s) such as blood vessels, the urinary tract, the intestinal tract, nasal cavity, neural sheath, bone cavity, kidney ducts, and those previously intervened body spaces that have implanted vascular grafts, stents, prosthesis', or other type of medical implants. The catheter balloon can be of the type with a catheter passing through a full length of the balloon, or of the type with a balloon placed at an end of a catheter. Additional examples include as a device for the removal of obstructions such as emboli and thrombi from blood vessels, as a dilation device to restore patency to an occluded body passage as an occlusion device to selectively deliver a means to obstruct or fill a passage or space, and as a centering mechanism for transluminal instruments and catheters. The radially expandable device 16 can also be used as a sheath for covering conventional catheter balloons to control the expansion of the conventional balloon. Furthermore, the radially expandable device 16 can be porous or non-porous, depending on the particular application.

The body of the example radially expandable device 16 is deployable upon application of an expansion force from a first, reduced diameter configuration, illustrated in FIG. 2, to a second, increased diameter configuration, illustrated in FIG. 3. The body of the radially expandable device 16 preferably features a monolithic construction, i.e., a singular, unitary article of generally homogeneous material. The example radially expandable device 16 can be, for example, manufactured using an extrusion and expansion process. In addition, the radially expandable device 16 is merely one example embodiment. Any therapeutic drug or agent delivery device capable of sustaining a desired elevated pressure as described below, some of which can deliver a fluid with a therapeutic drug or agent under pressure to an isolated location, as understood by one of ordinary skill in the art, can be utilized, depending on the particular application. As shown, the radially expandable device 16 is an expandable shape that can be coupled with a catheter or other structure, potentially able to provide fluid (in the form of a slurry of nanoparticles, semi-solid, solid, gel, liquid or gas, if fluid delivery is desired and the device is porous) to the radially expandable device 16. If the radially expandable device 16 is not porous, then the catheter can deliver a fluid (of a number of different types) to inflate the radially expandable device 16 and maintain a desired pressure. The material utilized for the radially expandable device 16 can be, for example, PTFE or PET, among other materials known to those of ordinary skill in the art, depending on the particular application desired.

The example process can yield a radially expandable device 16 characterized by a non-perforated seamless construction of inelastic, polyester nylon blend material. The nylon blend has a predefined size and shape in the second, increased diameter configuration. The radially expandable device 16 can be dependably and predictably expanded to the predefined, fixed maximum diameter and to the predefined shape independent of the expansion force used to expand the device.

The radially expandable device 16 is preferably generally tubular in shape when expanded, although other cross-sections, such as rectangular, oval, elliptical, or polygonal, can be utilized, depending on a particular application. The cross-section of the radially expandable device 16 is preferably continuous and uniform along the length of the body. However, in alternative embodiments, the cross-section can vary in size and/or shape along the length of the body. FIG. 2 illustrates the radially expandable device 16 relaxed in the first, reduced diameter configuration. The radially expandable device 16 has a central lumen extending along a longitudinal axis between two ends of the device.

A deployment mechanism in the form of an elongated hollow tube, such as the catheter 12, is shown positioned within the central lumen of the radially expandable device 16 to provide a radial deployment or expansion force to the radially expandable device 16. The radial deployment force effects radial expansion of the radially expandable device 16 from the first configuration to the second increased diameter configuration illustrated in FIG. 3. The radially expandable device 16 can be formed by thermal or adhesive bonding, or attached by other means suitable for inhibiting fluid leakage where unwanted.

The catheter 12 includes an internal, longitudinal extending lumen and a number of openings 28 that provide for fluid communication between the exterior of the catheter 12 and the lumen. The catheter 12 can be coupled to a fluid source or sources to selectively provide fluid to the radially expandable device 16 through the openings 28. The pressure from the fluid provides a radially expandable force on the body 12 to radially expand the body 12 to the second, increased diameter configuration. Because the body 12 is constructed from an inelastic material, uncoupling the tube 20 from the fluid source or otherwise substantially reducing the fluid pressure within the lumen 13 of the body 12, does not generally result in the body 12 returning to the first, reduced diameter configuration. However, the body 12 will collapse under its own weight to a reduced diameter. Application of negative pressure, from, for example, a vacuum source, can be used to completely deflate the body 12 to the initial reduced diameter configuration.

One skilled in the art will appreciate that the radially expandable device 16 is not limited to use with deployment mechanisms employing a fluid deployment force, such as the catheter 12. Other known deployment mechanisms can be used to radially deploy the radially expandable device 16 including, for example, mechanical operated expansion elements, such as mechanically activated members or mechanical elements constructed from temperature activated materials such as nitinol.

Various fluoropolymer materials are additionally suitable for use in the present invention. Suitable fluoropolymer materials include, for example, polytetrafluoroethylene ("PTFE") or copolymers of tetrafluoroethylene with other monomers may be used. Such monomers include ethylene, chlorotrifluoroethylene, perfluoroalkoxytetrafluoroethylene, or fluorinated propylenes such as hexafluoropropylene. PTFE is utilized most often. Accordingly, while the radially expandable device 16 can be manufactured from various fluoropolymer materials, and the manufacturing methods of the present invention can utilize various fluoropolymer materials, the description set forth herein refers specifically to PTFE. In addition, PET or polyester nylon blend can be utilized, depending on the desired material properties.

Turning now to an example application for the method of the present invention, a description of an angioplasty in accordance with the present invention will be described. In general, an angioplasty procedure is a procedure used to widen vessels narrowed by stenosis, restenosis, or occlusions. There are a number of different types of angioplasty procedures. In individuals with an occlusive vascular disease such as atherosclerosis, blood flow is impaired to an organ, such as the heart, or to a distal body part, such as an arm or leg, by the narrowing of the vessel's lumen due proliferation of a certain luminal cell type that has been impaired by vulnerable plaques, fatty deposits or calcium accumulation. The angioplasty procedure is a mechanical radial expansion procedure performed to radially open or widen the cross-sectional area of the vessel. Once the reperfusion procedure is completed, a desired blood flow returns within the mechanically opened area.

Over time, the vessel may constrict again, e.g., cellular proliferation called restenosis. The angioplasty procedure can be performed to re-open the vessel to a larger cross-sectional area. To prevent recoil or help control the occurrence or rate of restenosis, a stent can be implanted in the vessel. The stent is typically in the form of a radially expandable porous metal mesh tube, which following expansion forms a supporting scaffolding structure. As with any non-biological or foreign object or material in the body, like a stent or polymer coating, the risk of both acute and chronic inflammation and thrombosis is increased. Inflammation is due in part to the acute natural foreign body reaction. Inflammation caused by foreign body response is a primary reason why patients receive systemic medication, including, anti-inflammation, anti-proliferation, and anti-clotting medications before, during, and after interventional procedures, including stent implantations. However, such medications are not delivered specifically at the location of the injury to the vessel at the time of reperfusion injury or radial stent deployment into the vessel wall.

Generally, the implantation of a stent follows an angioplasty, but this is not always a requirement. For many patients, a direct stenting technique may be preferred to speed the reperfusion of the vessel, and to improve the delivery of the implant with a one step technique. In either instance, the stent is positioned in the vessel at the targeted tissue location by use of a deflated radially expandable balloon catheter. The radially expandable catheter device is inflated, expanding the stent against the vessel walls. The radially expandable catheter device is removed, leaving the stent in place in an expanded condition to mechanically hold the vessel open. Occasionally, another radially expandable balloon catheter device is inserted either entirely or partially into the previously stented vessel at the location of the stent and inflated to ensure the stent is properly expanded throughout so as to not migrate or move along the vessel wall, and to insure no gaps occur under the expanded stent, which are sources for excessive clot formation when not fully expanded.

In addition to the radially expandable device 16, FIG. 3 shows a therapeutic coating 30 applied to the radially expandable device 16. The therapeutic coating is applied to the medical device 10, in this case the radially expandable device 16, to create a therapeutic effect on the tissue at the targeted tissue location in a patient. The inclusion of the therapeutic coating 30 creates the opportunity to provide a medical or therapeutic effect for tissue that makes contact with the medical device 10. The therapeutic effect can be varied by the particular therapeutic agent incorporated into the therapeutic coating 30. The therapeutic coating 30 is made to coat the medical device 10 in a manner such that an efficacious amount of the therapeutic coating 30 does not wash away with bodily fluid passing by the medical device 10. The therapeutic coating 30 additionally will transfer from the medical device 10 to the targeted tissue location of the patient upon substantive contact with the medical device 10, and remain at or on the targeted tissue location to penetrate the tissue. The therapeutic coating can be applied to the radially expandable device 16, e.g., at a manufacturing stage, or just prior to insertion of the radially expandable device 16 into the body lumen.

In the following description of FIGS. 4, 5, and 6, methods are described for utilizing the radially expandable device 16 and the therapeutic coating 30. Each flowchart represents a different portion of a larger method. Each portion, as represented by each different flowchart, is a separate method, and there is no requirement that the three methods represented by the three flowcharts be practiced either together or in the particular order of the description. In addition, the description corresponding to the methods and the flowcharts refers to different instances of the radially expandable device 16, the therapeutic coating 30, the catheter 12, and the stent 14. Because it would be repetitive to show separate illustrations for each instance of these components, additional reference numbers are not provided for each instance. Thus, the radially expandable device 16, as referred to in the methods, can be the same device utilized in each of the methods, can be different instances of the same device, or can be different variations of similar devices to the radially expandable device 16 shown in FIGS. 2 and 3. Likewise, each reference to the other components can represent different instances of the same device, as would be understood by one of ordinary skill in the art.

Figure 4:
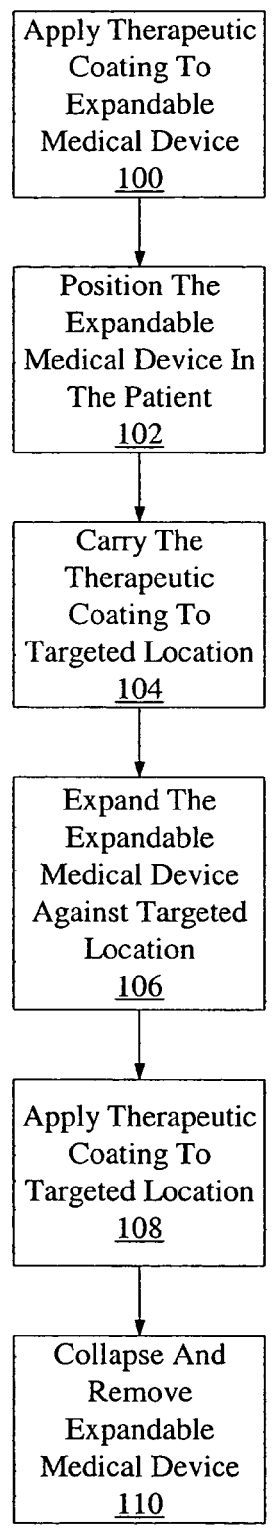
FIG. 4 is a flowchart showing a method of applying a therapeutic coating to a targeted tissue location, according to one aspect of the present invention.

FIG. 4 is a flowchart illustrating one example implementation of the present invention as applied to the angioplasty and stent procedures. A first therapeutic coating is applied to a first radially expandable device at some time prior to insertion into the vessel (step 100). A first catheter and the first radially expandable device are placed in a narrowed organ passageway (step 102). The first therapeutic coating is carried by the first radially expandable-device and delivered to a targeted tissue location where the first radially expandable device is targeted for expansion (step 104). The passageway is dilated from a first small diameter to a second larger diameter with the first radial expandable device, such as a balloon catheter (step 106). The first therapeutic coating is substantially uniformly applied or smeared onto and into the targeted tissue during the process of radial expansion of the first radially expandable device (step 108). The first radially expandable device is then deflated and removed (step 110), while a portion of the first therapeutic coating remains affixed onto and into the targeted tissue location following removal of the first radially expandable device.

Figure 5:
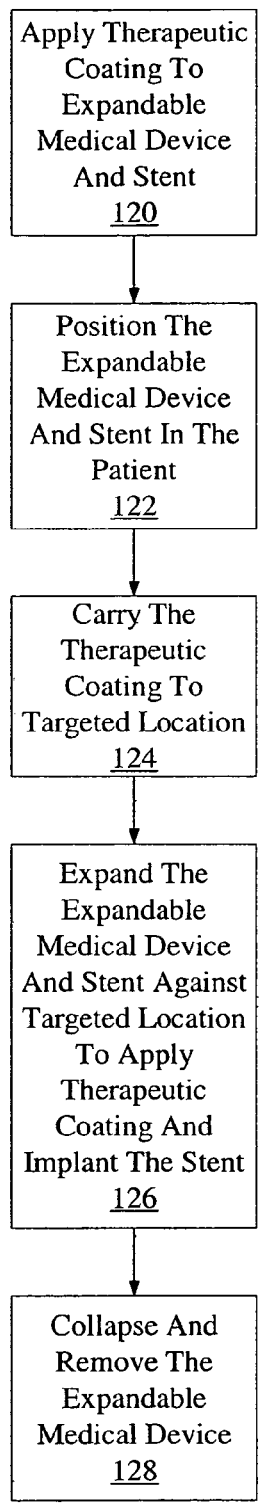
FIG. 5 is a flowchart showing another method of applying a therapeutic coating to a targeted tissue location, according to one aspect of the present invention.

FIG. 5 is a flowchart illustrating a further example implementation that can be carried out after the implementation of FIG. 4, or can be implemented regardless of the occurrence of the implementation of FIG. 4. In FIG. 5, a therapeutic intervention is performed. A second therapeutic coating is applied to both a second radially expandable device and a stent at some point in time prior to insertion into the body lumen (step 120). At least a portion of the second radially expandable device together with the crimped radially expandable stent is placed within or partly within the targeted tissue location of the first intervention (step 122). The second therapeutic coating is carried and delivered to the targeted tissue location by both the second radially expandable device and the radially expandable stent (step 124). A radial expansion and deployment of the second radially expandable device and the radially expandable stent uniformly applies and/or smears the second therapeutic coating onto and into the targeted tissue location treatment site (step 126) as the stent is deployed against the vessel wall. The second radially expandable device is then deflated and removed (step 128), while the radially expandable stent and a portion of the second therapeutic coating remains affixed onto and into the targeted tissue location.

Figure 6:
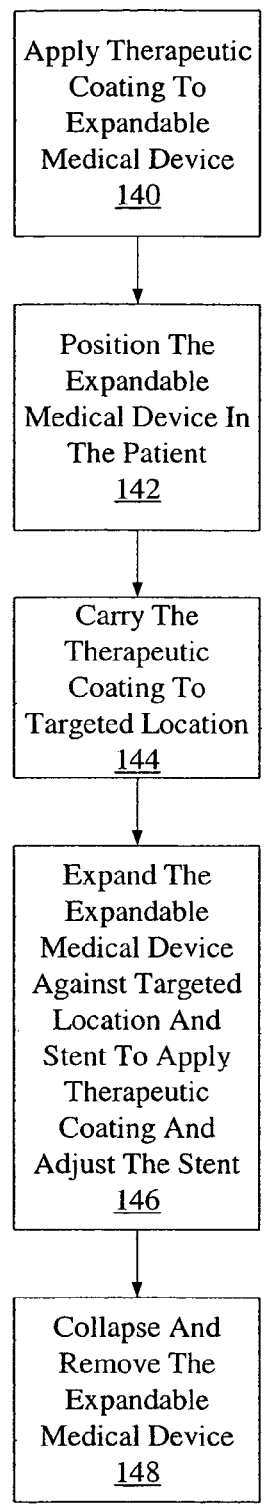
FIG. 6 is a flowchart showing another method of applying a therapeutic coating to a targeted tissue location, according to one aspect of the present invention.

FIG. 6 illustrates a third method that can be included in combination with one or both of the methods of FIGS. 4 and 5. A third therapeutic intervention is performed. A third therapeutic coating is applied to a third radially expandable device at some point in time prior to insertion into the body lumen (step 140). At least a portion of the third radially expandable device is placed within or partly within the targeted tissue location of the first intervention (step 142), in proximity to a stent, if a stent has been implanted. The third therapeutic coating is carried and delivered to the targeted tissue location the third radially expandable device (step 144). A radial expansion and deployment of the third radially expandable device uniformly applies and/or smears the third therapeutic coating onto and into the targeted tissue location treatment site (step 146) as the stent diameter expansion is adjusted to a desired final expansion amount. The third radially expandable device is then deflated and removed (step 148), while a portion of the third therapeutic coating remains affixed onto and into the targeted tissue location.

The methods of FIGS. 4, 5, and 6, can be performed in combination or individually as a complete procedure. As described herein, with a first, second, and third application of the therapeutic agent in the form of the therapeutic coating 30, maximum benefit is achieved from the particular therapeutic agent or agents utilized in the therapeutic coating 30. More specifically, in the example instance of an angioplasty followed by a stent implantation, the initial application of the therapeutic coating 30 is at the first intervention with the targeted tissue location. The therapeutic coating 30 is applied directly to the diseased artery to have an immediate therapeutic effect as the vessel is opened. The therapeutic coating 30 is again applied to the diseased artery targeted tissue location when the radially expandable device, smeared with the therapeutic coating 30, is utilized to introduce and expand a stent. The stent can likewise support at least some portion of the therapeutic coating 30 following expansion within the vessel. In such an arrangement, there is a therapeutic coating 30 over 100% of the cylindrical shape of the stent 14 and the radially expandable device 16, such as a balloon catheter. This is unlike conventional methods that only coat the stent with a drug eluting polymer coating that only allows the drug to migrate out of the polymer surface without a therapeutic agent transfer effect at the time of deployment. After the radially expandable device has been inflated and implanted the stent, the radially expandable device is removed. Then, if desired, a third intervention can introduce another radially expandable device, such as a balloon catheter, also having the therapeutic coating 30, for further radial expansion of the previously deployed stent. Again, upon expansion, the radially expandable device smears/applies the therapeutic coating 30 to the tissue and the stent at the targeted tissue location.

Regardless of the number of interventions performed oil a targeted tissue location in accordance with the method of the present invention, the end result should deliver a predetermined dosage of the therapeutic coating. Thus, if only one intervention is performed, a larger coating dosage can be required than if the intervention requires three or more distinct reperfusion steps.

As applied to the example angioplasty procedure, the present invention provides for an effective and efficient therapeutic agent or drug delivery, with more effective surface area coverage of the targeted tissue relative to known interventional drug eluting or systemic delivery procedures. The radially expandable devices expand from a first smaller diameter to a second larger diameter with a non-polymeric transferable therapeutic coating. Use of a therapeutic coating, agent, or biological material further aids in the transfer and tissue adhesion property of the material being applied directly onto and into the targeted treatment site during radial expansion of either the first intervention or second intervention, within or at least partially within the same targeted treatment sites.

During the three different intervention procedures, there are three opportunities for therapeutic coatings to be applied to the targeted tissue location. As such, there can be three different mixtures of therapeutic agents specifically designed to effect a desired targeted tissue or cellular response for each of the three stages of the radial expansion angioplasty/stent procedure. Likewise, as understood by one of ordinary skill in the art, the present invention is not limited to only three intervention procedures at the same targeted tissue location. Instead, there can be any number of different radially expandable interventional catheter procedures, each introducing a medical device 10 with a an atraumatic therapeutic coating 30 to effect a desired biological or therapeutic result at the targeted tissue location.

The therapeutic coating 30 can be applied to the medical device 10 utilizing a number of different processes. For example, the therapeutic coating 30 can be painted sprayed, or smeared, onto the medical device 10, and sterilized prior to clinical application or use. The entire sterile medical device 10 or a portion thereof, can be submerged into a container containing the sterile therapeutic coating. The sterile medical device 10 can be rolled in a sterile tray containing the therapeutic coating. Additional methods of applying the therapeutic coating to the medical device can involve heating, or drying, or combinations thereof. One of ordinary skill in the art will appreciate that the invention is not limited by the particular method of preparing the sterile medical device 10 with the sterile therapeutic coating 30. Instead, any number of different methods can be utilized to result with the therapeutic coating 30 applied to the medical device 10 in a manner that promotes transfer of the therapeutic coating 30 to a targeted tissue location within a patient upon intervention by the medical device 10.

The therapeutic coating 30 can be formed of a number of different agents and compositions. The therapeutic coating can be a non-polymeric, biologically compatible coating. The coating can be formed entirely of a single substance, or can be formed using a mixture, aggregate, compilation, composition, and the like, of two or more substances, including one or more different therapeutic agent nano-particles, one or more of which can be a therapeutic agent having therapeutic properties, and/or biological effects to the targeted tissue location.

In accordance with one example embodiment, the therapeutic coating can be formed of a non-polymeric, biologically compatible, oil or fat. There are a number of different therapeutic agents that are either lipophilic, or do not have a substantial aversion to oils or fats. Such therapeutic agents can be mixed with the oil or fat, without forming a chemical bond, and delivered to a targeted tissue location within a patient in accordance with the teachings of the present invention. Table 1, below, includes at least a partial listing of therapeutic agents that can be mixed with oils and fats for delivery to a targeted tissue location using a radially expandable interventional device.

TABLE #1

| CLASS | EXAMPLES |
|---|---|
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids, NSAIDS, ibuprofen, acetaminophen, hydrocortisone acetate, hydrocortisone sodium phosphate |
| Growth Factor Antagonists | Angiopeptin, trapidil, suramin |
| Antiplatelet Agents | Aspirin, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus microphenonol acid, rapamycin, everolimus, tacrolimus, paclitaxel, estradiol, dexamethasone, methatrexate, cilastozol, prednisone, cyclosporine, doxorubicin, ranpirnas, troglitzon, valsarten, pemirolast, pimecrolimus, SAR 943 |
| Tissue growth stimulants | Bone morphogeneic protein, fibroblast growth factor |
| Gasses | Nitric oxide, super oxygenated O2 |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estrogen, nitric oxide |

TABLE #1-continued

| CLASS | EXAMPLES |
|---|---|
| Second messenger targeting | Protein kinase inhibitors |
| Angiogenic | Angiopoetin, VEGF |
| Anti-Angiogenic | Endostatin |
| Inhibitation of Protein Synthesis | Halofuginone |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donative Derivatives | NCX 4016 - nitric oxide donative derivative of aspirin, snap |
| Gases | Nitric oxide, super oxygenated $O_2$ compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Chemotherapeutic Agents | Cyclosporine, doxorubicin, paclitaxel, tacrolimus, sirolimus, fludarabine, ranpirnase, zoledronic acid, imatinib mesylate (STI571/Gleevec) |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyalonic acid, human plasma derived surgical sealants, and agents comprised of hyaluronate and carboxymethylcellulose that are combined with dimethylaminopropyl, ethylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Protein Kinase Inhibitors | PKC 412 |

The act of mixing the therapeutic agent with the oil or fat results in a therapeutic mixture for application to the medical device 10 as a therapeutic coating. The therapeutic mixture can stick sufficiently well enough to the medical device, such as a delivery device or prosthesis, to transfer the therapeutic coating to a targeted tissue location within a patient following radial expansion of the device. An improved permeability of the tissue at the targeted tissue location by the oil or fat results in improved permeation by the therapeutic agent as well. In addition, a natural lipophilic tissue adherence characteristic of the oil or fat reduces the likelihood that most of the therapeutic mixture will be washed away by passing body fluids following placement of the device at the targeted tissue location. Therefore, the therapeutic mixture is held in place along the treatment area of the targeted tissue location, improving the permeation potential of the tissue by the mixture, and thus improving the therapeutic effect to the targeted treatment area within the body.

There are several oils and fats that are appropriate for use with the present invention. One fatty acid found to perform well was an omega 3 fatty acid, such as fish oil. Another component of the oils and fats found to function well with the present invention is alfa-tocopherol. There are a plurality of additional oils and fats and other components, some of which are listed in Table 2 below.

TABLE #2

Fish Oil
Cod-liver Oil
Squid Oil
Olive Oil
Linseed Oil
Sunflower Oil
Corn Oil
Palm/Palmnut Oil
Flax Seed Oil In addition, the mixture of therapeutic agent and oil or fat can include other components such as a solvent. The solvent serves to control or adjust the viscosity of the mixture. Other components such as a polymeric substance, a binder, and a viscosity increasing agent can be added to stabilize the therapeutic mixture or affect other characteristics of the mixture. Furthermore, the mixture itself can be modified, such as through hydrogenation.

The present invention relates to a plurality of combinations involving some form of therapeutic application of a therapeutic coating onto and into the targeted tissue location during use of a medical device supporting the therapeutic coating. Such combinations can include implantation procedures, such as a radial stent deployment procedure, to the same area location (within or partially within the same treatment location). The technique and device technology allows a multiple application step means to deliver more coating, medicated or therapeutic agent, or biological, over a larger surface area than can be applied solely by a single catheter step means, or by a single step means using solely a drug eluting stent means. Typically, a drug eluting stent has a surface area equal to no more than 20% of the vessel wall, and therefore cannot deliver a coating, medicated agent, or biological to more than 20% of the targeted tissue site. The method of the present invention provides a means to deliver more therapeutics over a larger treatment area.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the disclosed invention is reserved.

What is claimed is:

1. A method of treating a targeted tissue location, comprising:
    applying the therapeutic coating to a medical device;
    positioning the medical device proximal to a targeted tissue location within a patient; and
    atraumatically smearing the therapeutic coating against the targeted tissue location, thus transferring at least a portion of the therapeutic coating to adhere through a lipophilic absorptive action to the targeted tissue location, the coating remaining at the targeted tissue location, permeating the targeted tissue location, and reducing an inflammatory reaction by the targeted tissue location.

2. The method of claim 1, further comprising removing the medical device.

3. The method of claim 1, wherein the therapeutic coating comprises fatty acids including omega-3 fatty acids.

4. The method of claim 1, wherein a therapeutic agent is emulsified in the therapeutic coating.

5. The method of claim 1, wherein a therapeutic agent is suspended in the therapeutic coating.

6. The method of claim 1, wherein the therapeutic coating is at least partially hydrogenated.

7. The method of claim 1, wherein the therapeutic coating further comprises at least one of a non-polymeric substance, a binder, and a viscosity increasing agent to stabilize the therapeutic mixture.

8. The method of claim 1, wherein upon implantation, the therapeutic coating maintains one of a soft solid, gel, and viscous liquid consistency.

9. The method of claim 1, wherein the therapeutic coating further comprises a solvent.

10. The method of claim 1, wherein the medical device comprises at least one of an endovascular prosthesis, an intraluminal prosthesis, a shunt, a catheter, a surgical tool, a suture wire, a stent, and a local drug delivery device.

11. The method of claim 1, wherein a plurality of medical devices are utilized during a procedure to apply the therapeutic coating.

12. A method of treating a targeted tissue location, comprising:
    applying the therapeutic coating to a balloon catheter;
    positioning the balloon catheter proximal to a targeted tissue location within a patient in a first interventional procedure;
    atraumatically smearing the therapeutic coating against the targeted tissue location, thus transferring at least a portion of the therapeutic coating to adhere through a lipophilic absorptive action to the targeted tissue location during expansion of the balloon catheter; and
    removing the balloon catheter from the patient, the coating remaining at the targeted tissue location, permeating the targeted tissue location, and reducing an inflammatory reaction by the targeted tissue location.

* * * * *